United States Patent
Woodard et al.

(10) Patent No.: US 12,295,590 B2
(45) Date of Patent: May 13, 2025

(54) MIS OSTEOTOMY GUIDE

(71) Applicant: Wright Medical Technology, Inc., Memphis, TN (US)

(72) Inventors: Joseph Ryan Woodard, Memphis, TN (US); Kian-Ming Wong, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 456 days.

(21) Appl. No.: 17/756,926

(22) PCT Filed: Jan. 6, 2021

(86) PCT No.: PCT/US2021/012247
§ 371 (c)(1),
(2) Date: Jun. 6, 2022

(87) PCT Pub. No.: WO2021/162805
PCT Pub. Date: Aug. 19, 2021

(65) Prior Publication Data
US 2023/0018466 A1   Jan. 19, 2023

Related U.S. Application Data (60) Provisional application No. 62/972,311, filed on Feb. 10, 2020.

(51) Int. Cl.
*A61B 17/15* (2006.01)
*A61B 17/17* (2006.01)
(Continued)

(52) U.S. Cl.
CPC ........ *A61B 17/151* (2013.01); *A61B 17/1775* (2016.11); *A61B 17/66* (2013.01); *A61B 17/848* (2013.01)

(58) Field of Classification Search
CPC . A61B 17/151; A61B 17/1775; A61B 17/152; A61B 17/15
See application file for complete search history.

(56) References Cited

U.S. PATENT DOCUMENTS 11,889,998 B1 * 2/2024 Treace ................. A61B 17/685
2011/0015636 A1   1/2011 Katrana et al.
(Continued)

FOREIGN PATENT DOCUMENTS

AU   2013260048 B2   7/2017
AU   2019246771 A1   10/2019

OTHER PUBLICATIONS

Extended European Search Report issued in connection with European Patent Application No. 21754046.7, Nov. 13, 2023, 8 pages.
(Continued)

*Primary Examiner* — Andrew Yang
(74) *Attorney, Agent, or Firm* — DUANE MORRIS LLP (57) ABSTRACT

A surgical guide includes a body defining a first access port and a second access port. The first access port extends on a first longitudinal access parallel with a first edge of the body and the second access port extends on a second longitudinal access positioned non-parallel with respect to each edge of the body. At least one coupling arm extends from the body. The at least one coupling arm defines at least one fixation aperture sized and configured to receive a fixation element through.

16 Claims, 13 Drawing Sheets

(51) Int. Cl.
    *A61B 17/66* (2006.01)
    *A61B 17/84* (2006.01)

(56) References Cited

U.S. PATENT DOCUMENTS

| | | |
|---|---|---|
| 2016/0199076 A1 | 7/2016 | Fallin et al. |
| 2017/0079669 A1* | 3/2017 | Bays .................. A61B 17/8866 |
| 2019/0099189 A1 | 4/2019 | Fallin et al. |
| 2019/0336140 A1 | 11/2019 | Dacosta et al. |

OTHER PUBLICATIONS

International Search Report and Written Opinion for PCT/US2021/012247 issued Mar. 25, 2021, 18 pages.

\* cited by examiner

MIS OSTEOTOMY GUIDE

CROSS-REFERENCE TO RELATED APPLICATION

This application is a National Stage Application, filed under 35 U.S.C. 371, of International Patent Application No. PCT/US2021/012247, filed on Jan. 6, 2021, which claims priority to U.S. Provisional Patent Application No. 62/972,311, filed on Feb. 10, 2020, the entireties of which are incorporated herein by reference.

BACKGROUND

Hallux valgus deformities in the human foot relate to a condition in which the first (great) toe has a deviated position leaning in towards the second toe. The first metatarsal deviates towards the mid-sagittal plane, and the great toe deviates away from the mid-sagittal plane. This is often accompanied by a bump due to a swollen bursal sac or a bony anomaly on the metatarsophalangeal joint.

A variety of non-surgical methods are used to treat hallux valgus, but in cases of continued pain or visible deformity, the patient may seek a surgical correction of the condition. Surgical methods may include removing the bony enlargement of the first metatarsal, realigning the first metatarsal bone relative to the adjacent metatarsal bone, and/or straightening the great toe relative to the first metatarsal and adjacent toes.

One such method of treating hallux valgus deformities is known as a Lapidus procedure. In a Lapidus procedure the first tarsal-metatarsal joint is fused to decrease the movement of the joint. This straightens the first metatarsal and toe to reduce or eliminate the hallux valgus deformity.

SUMMARY

In various embodiments, a surgical guide is disclosed. The surgical guide includes a body defining a first access port and a second access port. The first access port extends on a first longitudinal axis parallel with a first edge of the body and the second access port extends on a second longitudinal axis positioned non-parallel with respect to each edge of the body. At least one coupling arm extends from the body and defines at least one fixation aperture sized and configured to receive a fixation element through.

In various embodiments, a system is disclosed. The system includes a surgical guide, at least one fixation element, and a cutting instrument. The surgical guide includes a body defining a first access port and a second access port. The first access port extends on a first longitudinal access parallel with a first edge of the body and the second access port extends on a second longitudinal access positioned non-parallel with respect to each edge of the body. At least one coupling arm extends from the body and defines at least one fixation aperture. The at least one fixation element sized and configured to be received within the at least one fixation aperture. The cutting instrument is sized and configured for insertion through at least one of the first access port and the second access port.

In various embodiments, a surgical method is disclosed. The method includes a step of coupling a surgical guide to a first bone. The surgical guide includes a body defining a first access port and a second access port. The first access port extends on a first longitudinal access parallel with a first edge of the body and the second access port extends on a second longitudinal access positioned non-parallel with respect to each edge of the body. At least one coupling arm extends from the body and defines at least one fixation aperture. A cutting instrument is inserted through the first access port of the body to debride a joint and the surgical guide is coupled to a second bone. A cutting instrument is inserted through the second access port of the body to form an osteotomy in the second bone.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

Figure 1:
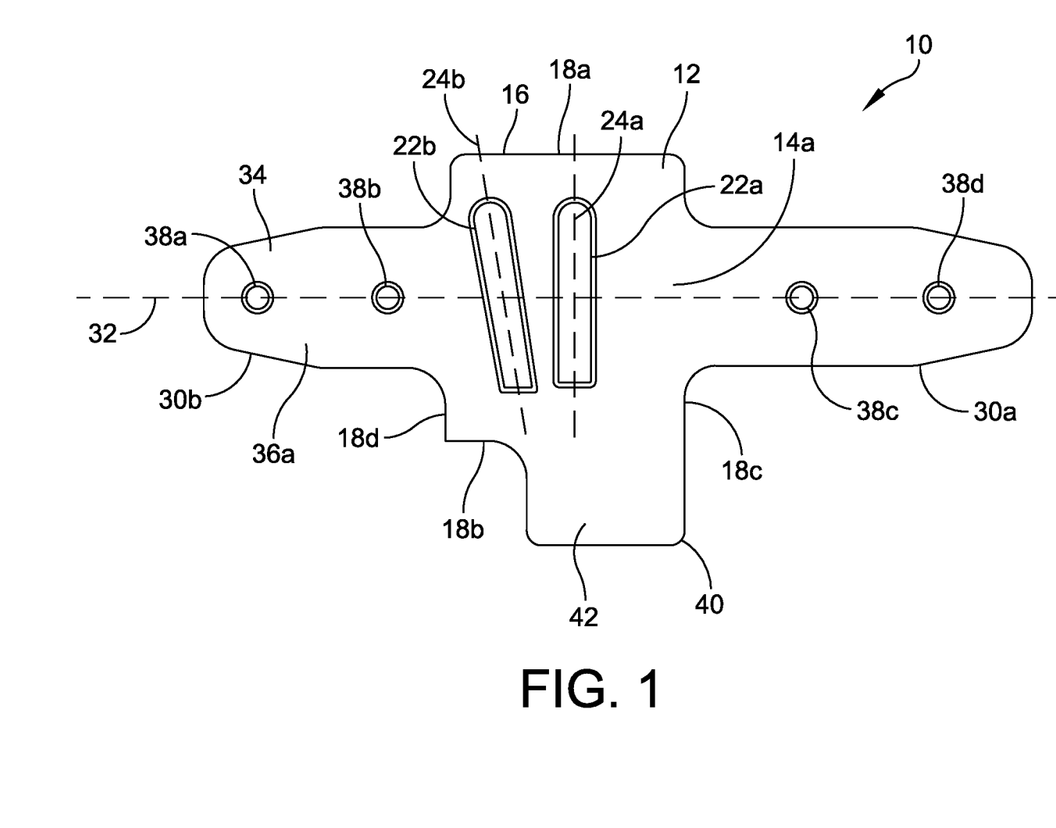
FIG. 1 illustrates a surgical guide configured for use in an osteotomy or arthrodesis procedure, in accordance with some embodiments.

FIG. 1 illustrates a surgical guide 10, in accordance with some embodiments. The surgical guide 10 is configured for use in a corrective procedure, such as, for example, a Lapidus procedure. The surgical guide 10 is configured to be coupled to one or more bones and guide insertion of one or more cutting instruments to form one or more osteotomies in the one or more bones. A method of using the surgical guide 10 to perform an osteotomy for a Lapidus procedure is described in greater detail with respect to FIGS. 4-12.

The surgical guide 10 includes a body 12 having a thickness extending between a first side 14a and a second side 14b. A perimeter wall 16 extends between the first side 14a and the second side 14b. In the illustrated embodiment, the perimeter wall 16 defines a generally rectangular shape having a front wall 18a, a back wall 18b, a first side wall 18c, and a second side wall 18d (collectively "perimeter walls 18"). The front wall 18a and the back wall 18b are substantially parallel. Similarly, the first side wall 18c and the second side wall 18d are substantially parallel and are each substantially perpendicular to the front wall 18a and the back wall 18b. Although specific embodiments are illustrated herein, it will be appreciated that the surgical guide can include "left" and "right" versions of the surgical guide, a "universal" version of the surgical guide, surgical guides omitting certain discussed features, and/or surgical guides having different shapes as those illustrated herein. All such variations are within the scope of this disclosure.

The body 12 defines at least access port 22a, 22b, extending from the first side 14a to the second side 14b. In the illustrated embodiment, the body includes a first access port 22a and a second access port 22b, although it will be appreciated that a greater and/or lesser number of slots may be defined by the body 12. The first access port 22a defines a slot extending along a first longitudinal axis 24a that is generally parallel to the side walls 18c, 18d of the body 12 and perpendicular to the front wall 18a and the back wall 18b. The second access port 22b defines a slot extending along a second longitudinal axis 24b that is set at an angle with respect to each of the walls 18 of the body 12. For example, in the illustrated embodiment, the second access port 22b is set at an angle between 15-75° with respect to each of the walls 18, although it will be appreciated that the first access port 22a and/or the second access port 22b may be defined at any suitable angle with respect to any of the walls 18.

In some embodiments, each of the access ports 22a, 22b are sized and configured to receive a cutting instrument, such as a burr, saw blade, drill bit, etc., therein. The access ports 22a, 22b are configured to guide the cutting instrument along a predetermined path when the surgical guide 10 is coupled to one or more bones. For example, as discussed in greater detail below, in some embodiments when the surgical guide 10 is coupled to a first bone and a second bone, the first access port 22a is configured to guide a cutting instrument to prepare a joint between the first bone and the second bone and the second access port 22b is configured to guide a cutting instrument to cut the second bone. Although specific embodiments are discussed herein, it will be appreciated that the access ports 22a, 22b may be arranged to guide any suitable cutting or other surgical operation.

In some embodiments, the surgical guide 10 includes a first coupling arm 30a and a second coupling arm 30b. The first coupling arm 30a extends from the first side wall 18c of the body 12. Similarly, the second coupling arm 30b extends from the second side wall 18d of the body 12. In the illustrated embodiment, each of the first coupling arm 30a and the second coupling arm 30b extend substantially along a longitudinal axis 32 extending substantially perpendicular to the first side wall 18c and the second side wall 18d. Although specific embodiments are illustrated, it will be appreciated that the coupling arms 30a, 30b may extend at any suitable angle with respect to the one or more walls 18 of the body 12.

Each of the coupling arms 30a, 30b include a body 34 extending between a first surface 36a and a second surface 36b. Each coupling arm 30a, 30b includes a perimeter wall 36. In the illustrated embodiment, each coupling arm 30a, 30b defines a substantially rounded rectangular shape, although it will be appreciated that each coupling arm 30a, 30b may have any suitable shape. The coupling arms 30a, 30b may be formed integrally with the body 12 and/or may be coupled to the body 12 using any suitable coupling mechanism.

In some embodiments, each of the coupling arms 30a, 30b define a plurality of fixation apertures 38a-38d (collectively "fixation apertures 38") extending from the first surface 36a to the second surface 36b. Each of the fixation apertures 38 is sized and configured to receive a fixation element therethrough. For example, in various embodiments, the fixation apertures 38 may be sized and configured to receive a k-wire, fixation wire, olive wire, screw, and/or other fixation element therethrough. In the illustrated embodiment, the fixation apertures 38 are substantially positioned along a single longitudinal line, although it will be appreciated that one or more of the fixation apertures 38 may be staggered with respect to a central longitudinal axis 32 of the coupling arms.

In some embodiments, a lateral wing 40 extends from the body 12. In the illustrated embodiment, the lateral wing 40 extends from the back wall 18b of the body, although it will be appreciated that the lateral wing 40 may extend from any suitable portion of the body 12, such as, for example, any of the walls 18. In some embodiments, the lateral wing 40 extends at an angle with respect to the body 12. For example, in the illustrated embodiment, the lateral wing 40 is substantially perpendicular to the body 12 (e.g., extends at an angle of about 90° with respect to the first surface 14a of the body 12). Although specific embodiments are discussed herein, it will be appreciated that the lateral wing 40 can extend at any suitable angle with respect to the body 12, such as, for example, 15-165°, 30-150°, 45-135°, 60-120°, and/or any other suitable range.

The lateral wing 40 includes a body 42 extending between a first surface 44a and a second surface 44b. The lateral wing 40 includes a perimeter wall 46 defining an outer perimeter of the body 42. In the illustrated embodiment, the lateral wing 40 includes a substantially rounded rectangular shape, although it will be appreciated that the lateral wing 40 may define any suitable shape.

In some embodiments, the lateral wing 40 defines an access port 22c (e.g., a third access port) extending from the first surface 44a to the second surface 44b (collectively with the access ports 22a, 22b "the access ports 22"). The access port 22c generally extends longitudinally along a longitudinal axis 50 and is sized and configured to receive a cutting instrument, such as a burr, saw blade, drill bit, etc., therethrough. The access port 22c guides the cutting instrument to form one or more cuts in a bone, joint space, and/or other anatomic structure when the surgical guide 10 is coupled to one or more bones. In some embodiments, the access port 22c is aligned with the access port 22a formed in the body 12 such that cuts made through the access port 22c are formed in the same plane as cuts made through the access port 22a. In some embodiments, the longitudinal axis 24a and the longitudinal axis 50 define the shared plane.

In some embodiments, the lateral wing 40 defines one or more fixation apertures 52a-52d (collectively "fixation apertures 52"). Each of the fixation apertures 52 are sized and configured to receive a fixation element therethrough, such as, for example, a fixation wire (e.g., k-wire, olive wire, etc.), screw, and/or other suitable fixation element. In some embodiments, each of the fixation apertures 52 define a hole axis extending through the lateral wing 40 that is perpendicular to a hole axis defined by the fixation apertures 38, although it will be appreciated that one or more of the hole axes can be angled with respect to any one or more of the other hole axes.

In some embodiments, one or more of the access ports 22 may be replaced with one or more holes, a plurality of slots, and/or other openings allowing access to a surgical site. For example, FIGS. 3 and 4 (discussed below) disclose embodiments including a tapered slot and an access port configured to provide access to a surgical site. As another example, in some embodiments, one or more of the access ports 22 may be replaced with a plurality of slots. The plurality of slots may be aligned on a common longitudinal axis.

In some embodiments, a guide element (not shown), such as a guide carriage, may be inserted into one of the access ports 22 prior to insertion of a cutting instrument, such as a burr. The guide element may be configured to limit motion of the cutting instrument in one or more directions (or planes). For example, in some embodiments, a guide carriage may be coupled to one of the access ports 22 to limit out-of-plane motion of a burr during debriding of a joint space and/or during formation of an osteotomy.

In some embodiments, the surgical guide 10 may include one or more radiolucent sections (or portions) and/or one or more radiopaque sections (or portions). The radiolucent and radiopaque sections are configured to allow imaging of the surgical guide 10 during and/or after positioning and fixation of the surgical guide with respect to at least one bone. For example, in some embodiments, the surgical guide 10 may be positioned adjacent to a first bone and a second bone (e.g., in contact with skin positioned adjacent to the first bone and the second bone). Radioscopic imaging may be performed to verify the position and alignment of the surgical guide 10 prior to insertion of fixation elements to fix the surgical guide 10 in place. As another example, radioscopic imaging may be performed after fixation of the surgical guide 10 but prior to and/or simultaneous with insertion of a cutting instrument to verify positioning and alignment of the surgical guide 10 for use in a cutting operation.

Figure 2:
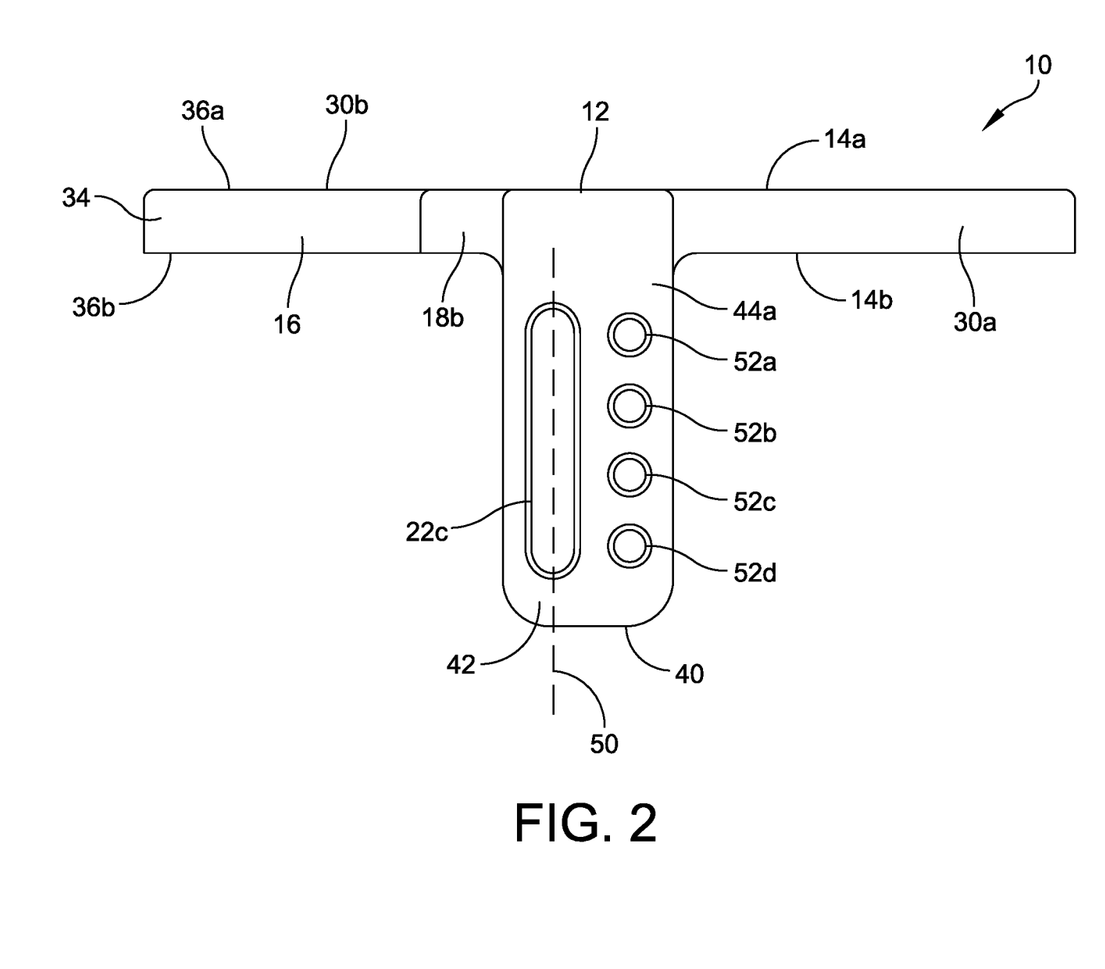
FIG. 2 illustrates a side view of the surgical guide of FIG. 1, in accordance with some embodiments.
Figure 3:
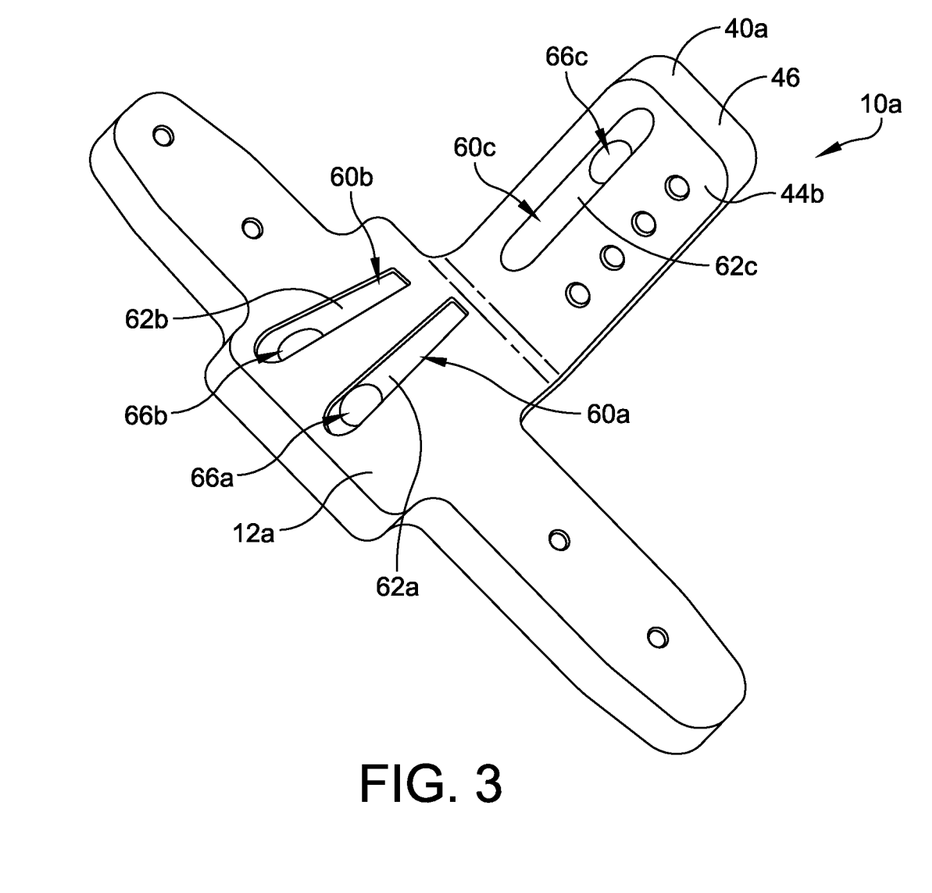
FIG. 3 illustrates a surgical guide having a plurality of tapered access ports, in accordance with some embodiments.

FIG. 3 illustrates an embodiment of a surgical guide 10a including tapered slots 60a-60c defined in the body 12a and the lateral wing 40a, in accordance with some embodiments. The surgical guide 10a is similar to the surgical guide 10 described above in conjunction with FIGS. 1-2, and similar description is not repeated herein. The surgical guide 10a includes a plurality of tapered access ports 60a-60c (collectively "tapered access ports 60"). Each of the tapered access ports 60 defines a tapered surface 62a-62c extending from a first end 64a of the tapered access port 60a-60c to an opening 66a-66c adjacent to a second end 64b of the access port 60a-60c. Each tapered surface 62a-62c is sized and configured to guide a cutting instrument, such as a burr, saw blade, drill bit, etc., into the opening 66a-66c. Each of the access ports 60 is sized and configured to allow pivoting of the cutting instrument within at least one plane. In some embodiments, the tapered surface 62a-62c and the opening 66a-66c cooperatively define the cutting range of a cutting instrument positioned within the access port 60.

Figure 4:
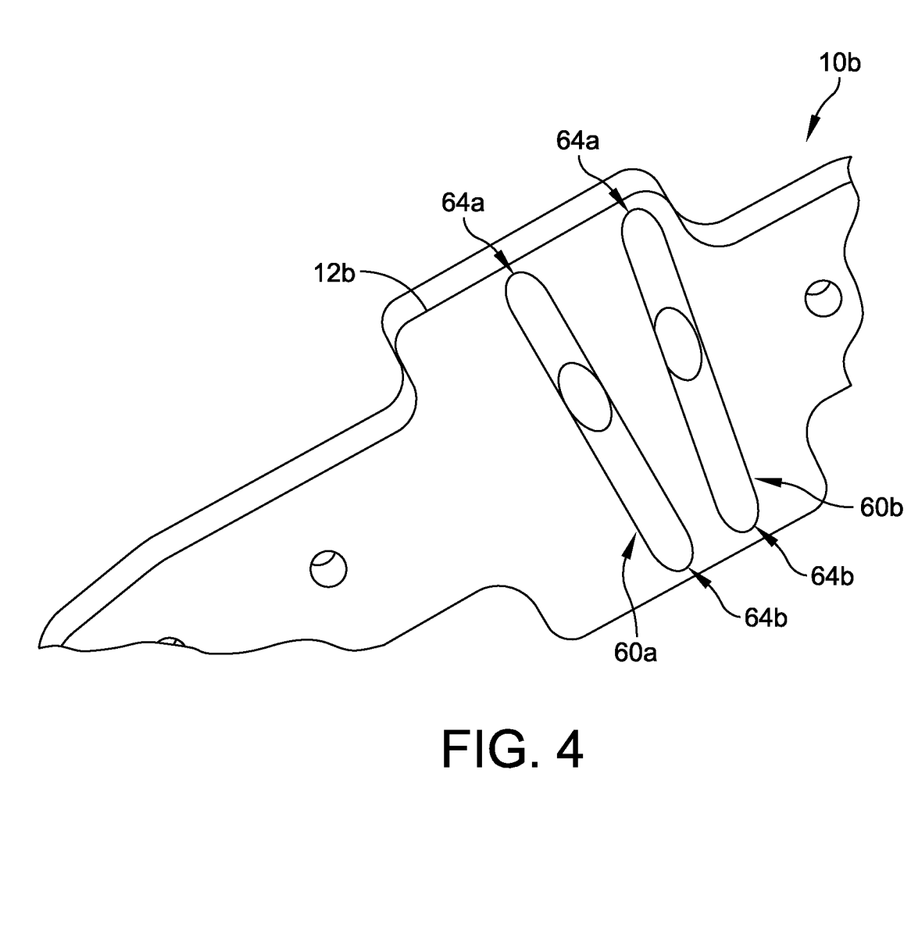
FIG. 4 illustrates a surgical guide having a plurality of tapered access ports in the body and lateral wing, in accordance with some embodiments.

FIG. 4 illustrates an embodiment of a surgical guide 10b without a lateral wing, in accordance with some embodiments. The surgical guide 10b is similar to the surgical guide 10a described in conjunction with FIG. 3 and similar description is not repeated herein. The surgical guide 10b omits the lateral wing 40, relying solely on the access ports 60a, 60b defined in the body 12b to perform one or more cutting operations in a bone coupled to the surgical guide 10b. In some embodiments, omitting the lateral wing 40 allows the surgical guide 10b to be positioned using a smaller incision, displacing less internal tissue, and/or allowing additional manipulation of the surgical guide 10b.

Figure 5:
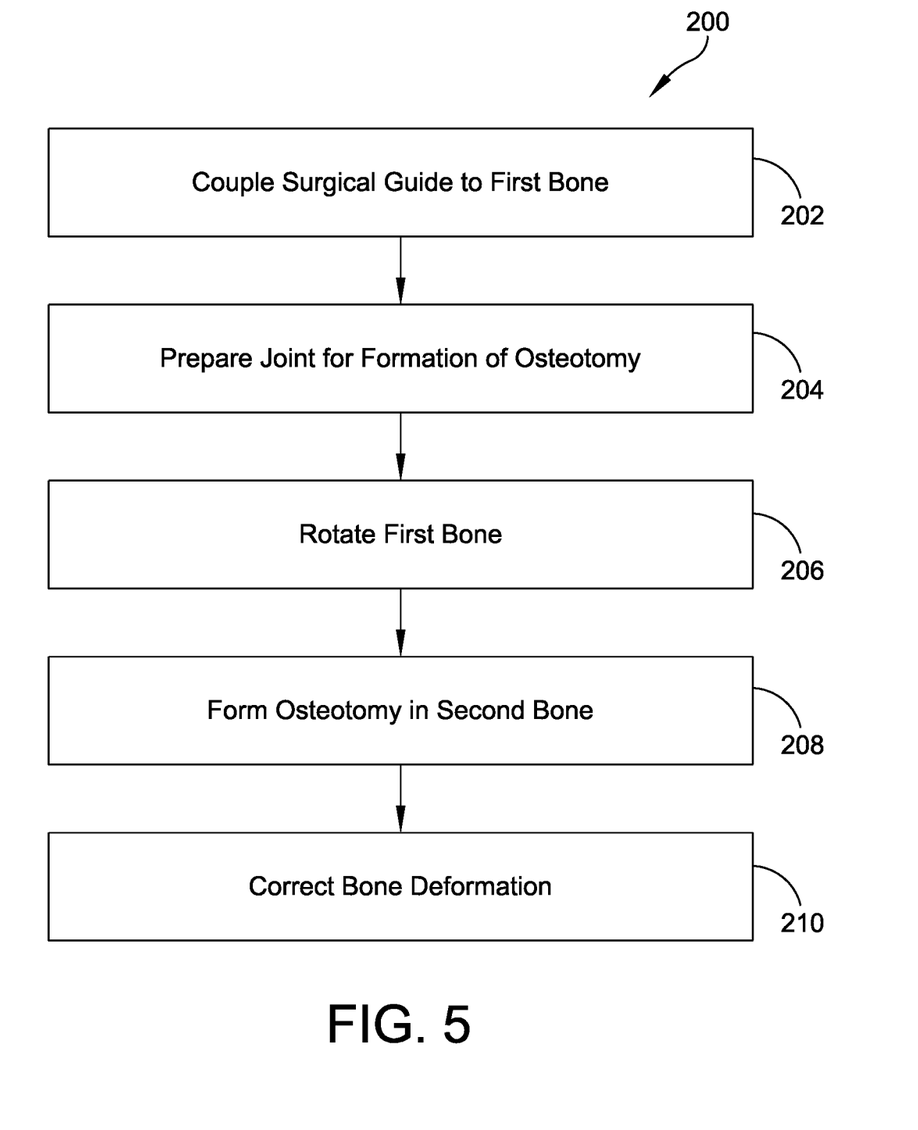
FIG. 5 is a flowchart illustrating a method of forming an osteotomy in a first bone, in accordance with some embodiments.

FIG. 5 is a flowchart illustrating a method 200 of forming an osteotomy using a surgical guide as disclosed and described herein. FIGS. 6-11 illustrate various steps of the method 200 using the surgical guide 10 described in conjunction with FIGS. 1-2. Although FIGS. 6-13 are illustrated using the surgical guide 10, it will be appreciated that the method 200 of forming an osteotomy may be implemented using any of the surgical guides 10, 10a, 10b and/or variations of the surgical guides 10, 10a, 10b described herein. Further, although the method of forming an osteotomy is shown with respect to foot 102, specifically a first metatarsal 104 and a medial cuneiform 106, it will be appreciated that the surgical guide 10 may be used to form an osteotomy in any suitable bone or bones. It will further be appreciated that the illustrated surgical guides may be used for other surgical procedures, such as, for example, a bunion procedure.

Figure 6:
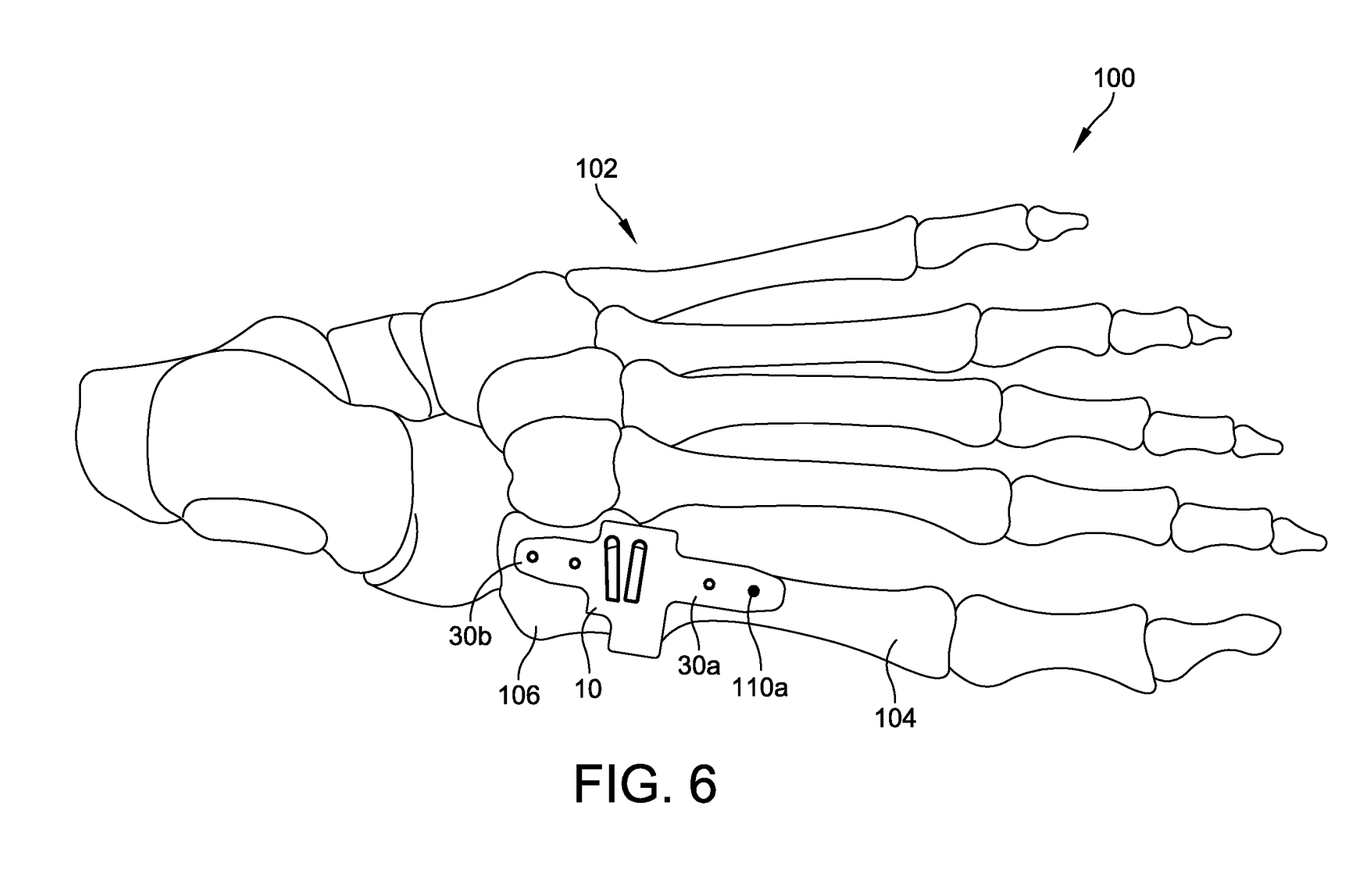
FIG. 6 illustrates the surgical guide of FIG. 1 coupled to a surgical site, in accordance with some embodiments.
Figure 7:
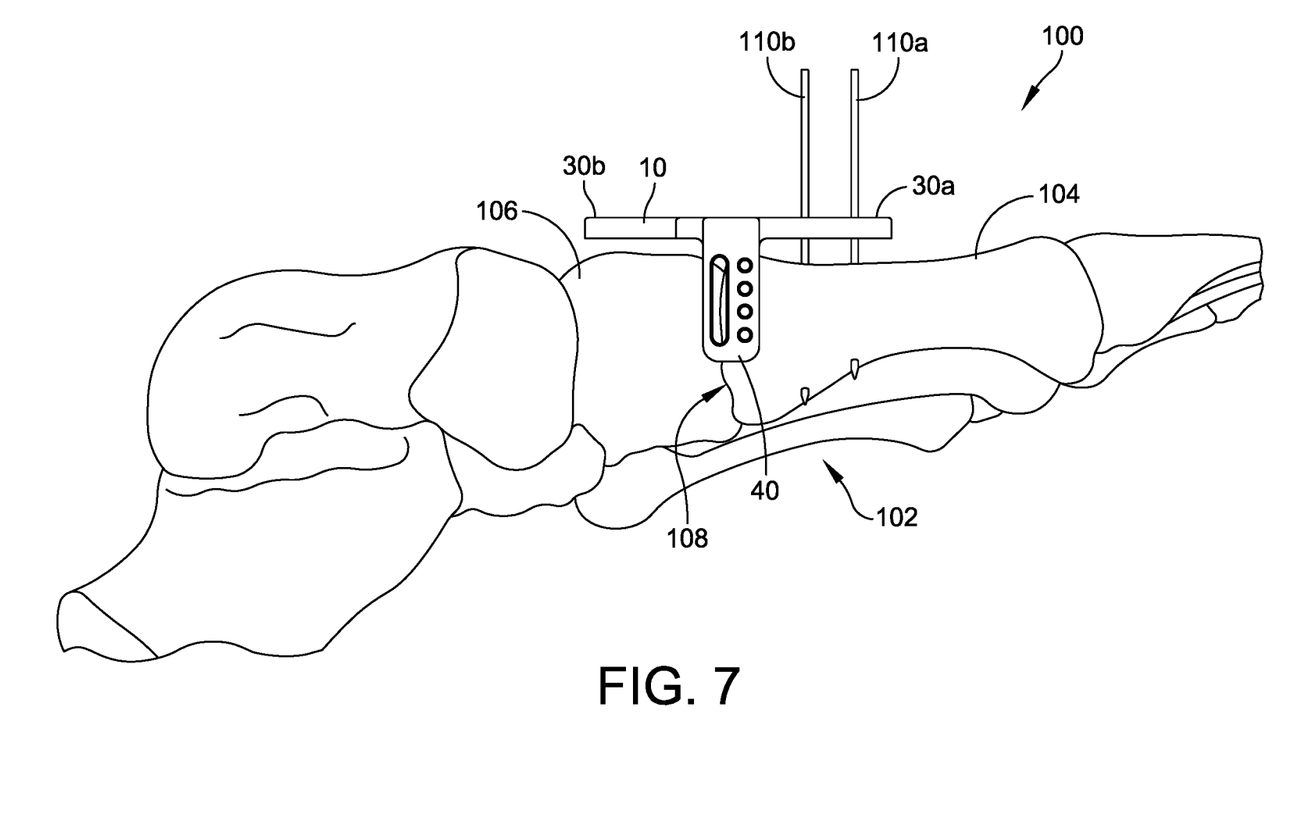
FIG. 7 illustrates a lateral view of the surgical site illustrated in FIG. 6, in accordance with some embodiments.

At step 202, as illustrated in FIGS. 6-7, a surgical guide 10 is coupled to a surgical site 100 such that the surgical guide 10 extends across a joint between a first bone and a second bone, such as, for example, a first metatarsal 104 and a medial cuneiform 106. The surgical guide 10 may be positioned such that the first access port 22a defined in the body 12 and/or the access port 22c defined in a lateral wing 40 is aligned with a joint 108 between the first metatarsal 104 and the medial cuneiform 106. The surgical guide 10 may be coupled to at least one of the bones, such as the first metatarsal 104, using any suitable fixation element. For example, in the illustrated embodiment, the surgical guide 10 is coupled to the first metatarsal 104 by a first k-wire 110a and a second k-wire 110b, although it will be appreciated that any suitable fixation element, such as a k-wire, olive wire, screw, nail, etc., may be used. The k-wires 110a, 110b are inserted through a respective fixation aperture 34 defined in a first coupling arm 30a of the surgical guide 10.

Figure 8:
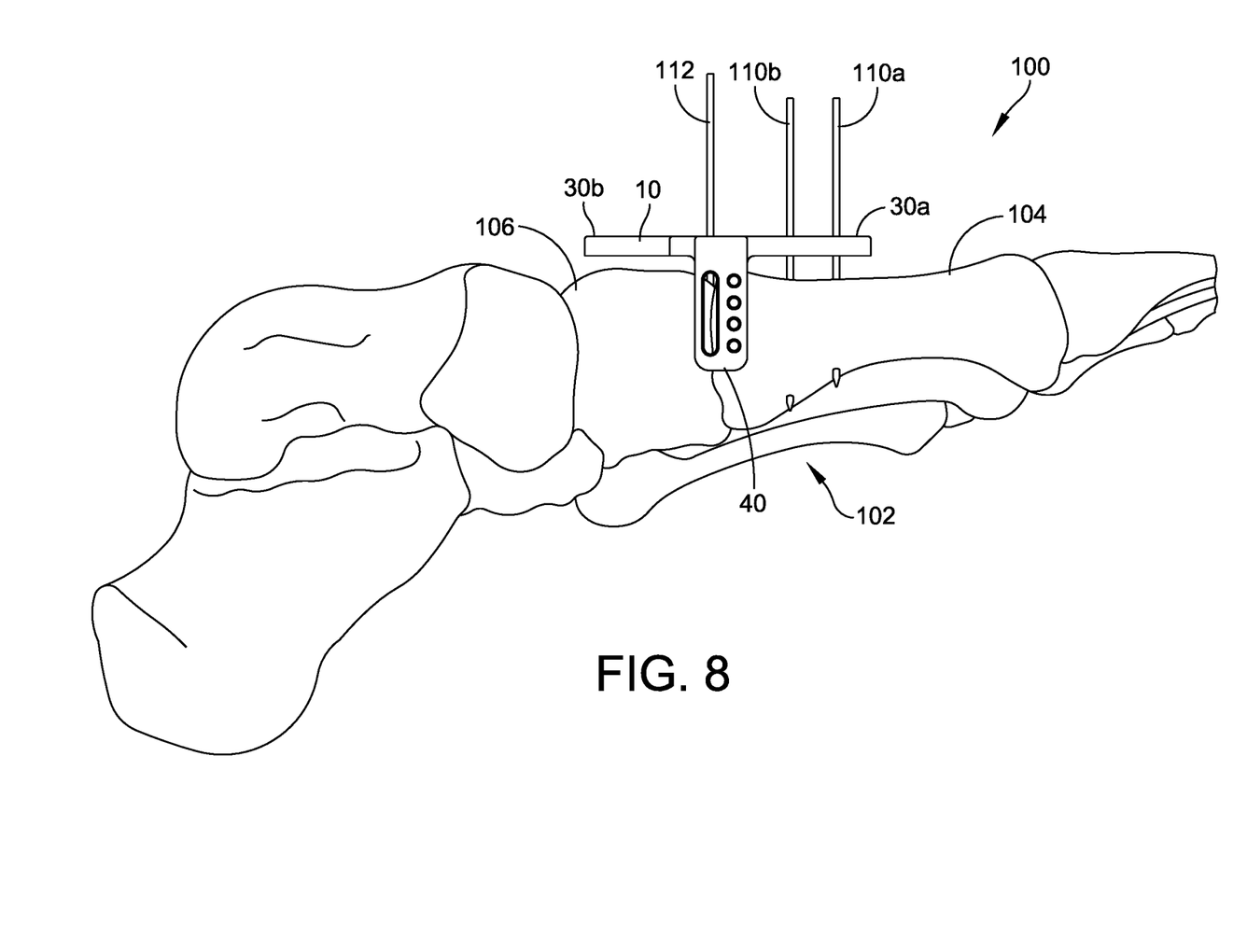
FIG. 8 illustrates a cutting instrument inserted through a slot defined in a lateral wing of the surgical guide, in accordance with some embodiments.
Figure 9:
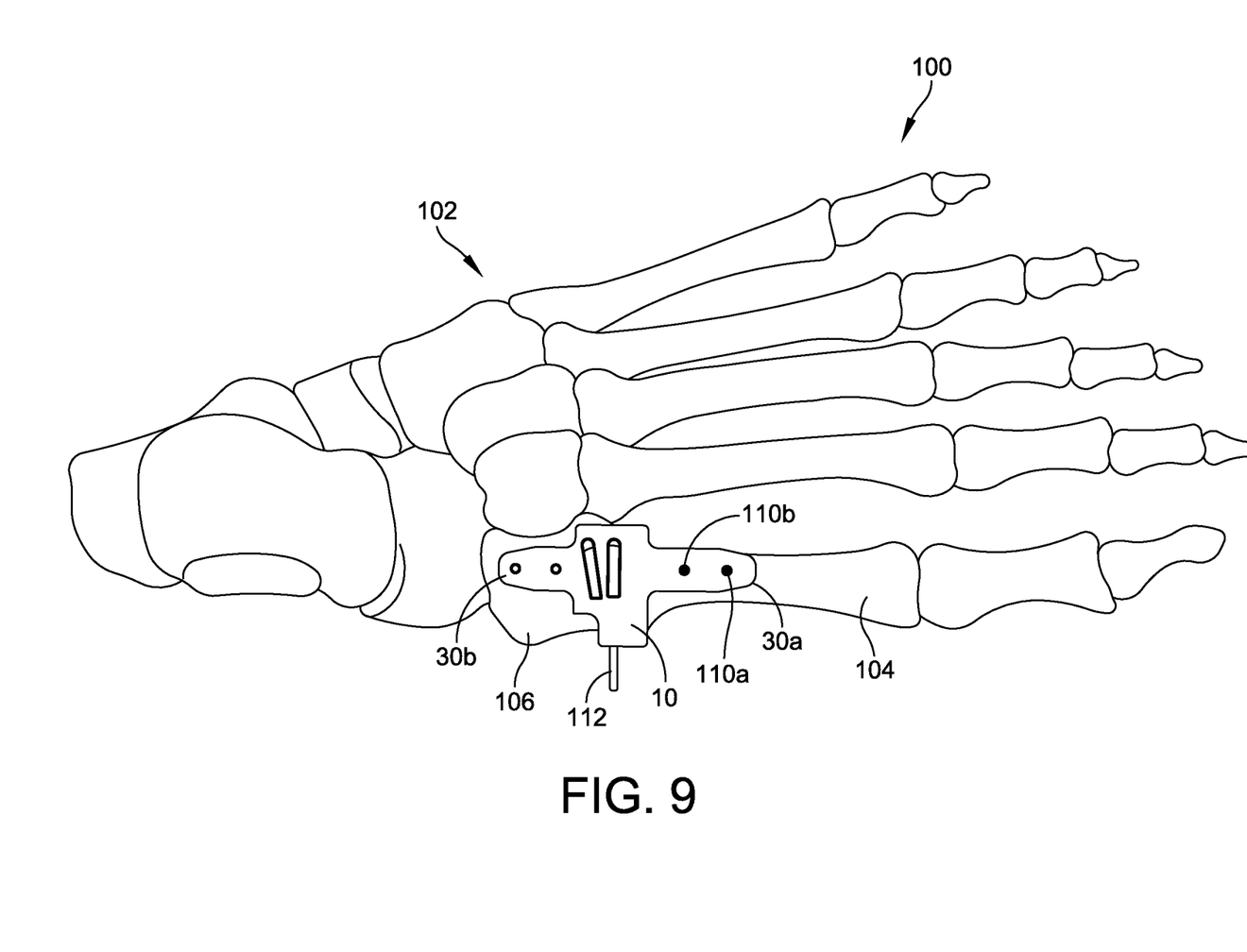
FIG. 9 illustrates a dorsal and plantar (D-P) view of the surgical site having the burr inserted through a first slot defined in the body of the surgical guide, in accordance with some embodiments.

At step 204, as illustrated in FIGS. 8-9, the joint 108 is prepared for formation of an osteotomy by inserting a cutting instrument, such as a burr 112, through one or more of the access ports 22 formed in the surgical guide 10. As illustrated in FIG. 8, the burr 112 is inserted through a first access port 22a formed in the body 12 of the surgical guide 10 (see FIG. 1). The burr 112 is inserted into the joint 108 to remove portions of the first metatarsal 104, the medial cuneiform 106, and/or tissue within the joint 108. As illustrated in FIG. 9, the burr 112 may also be inserted through the access port 22c formed in the lateral wing 40 to perform additional cutting and/or removal within the joint 108. In some embodiments, the first access port 22a and the third access port 22c are aligned such that cuts formed through either of the access ports 22a, 22c are formed in a single plane (e.g., a plane containing the joint 108).

The burr 112 may be inserted into a slot, such as access ports 22a or access port 22c, and manipulated to form one or more cuts. For example, in the illustrated embodiment, the burr 112 may be laterally translated along a longitudinal axis 24, 50 of the respective access port 22a, 22c and/or pivoted within the respective access port 22a, 22c to form respective cuts. In other embodiments, the burr 112 may be limited to a single form of movement. For example, the surgical guide 10a (as illustrated in FIG. 3) includes tapered access ports 60 configured to limit movement of a burr 112 during insertion and cutting operations. Although embodiments are discussed herein including burr 112, it will be appreciated that any suitable cutting instrument may be used to form cuts in the respective bones 104, 106.

Figure 10:
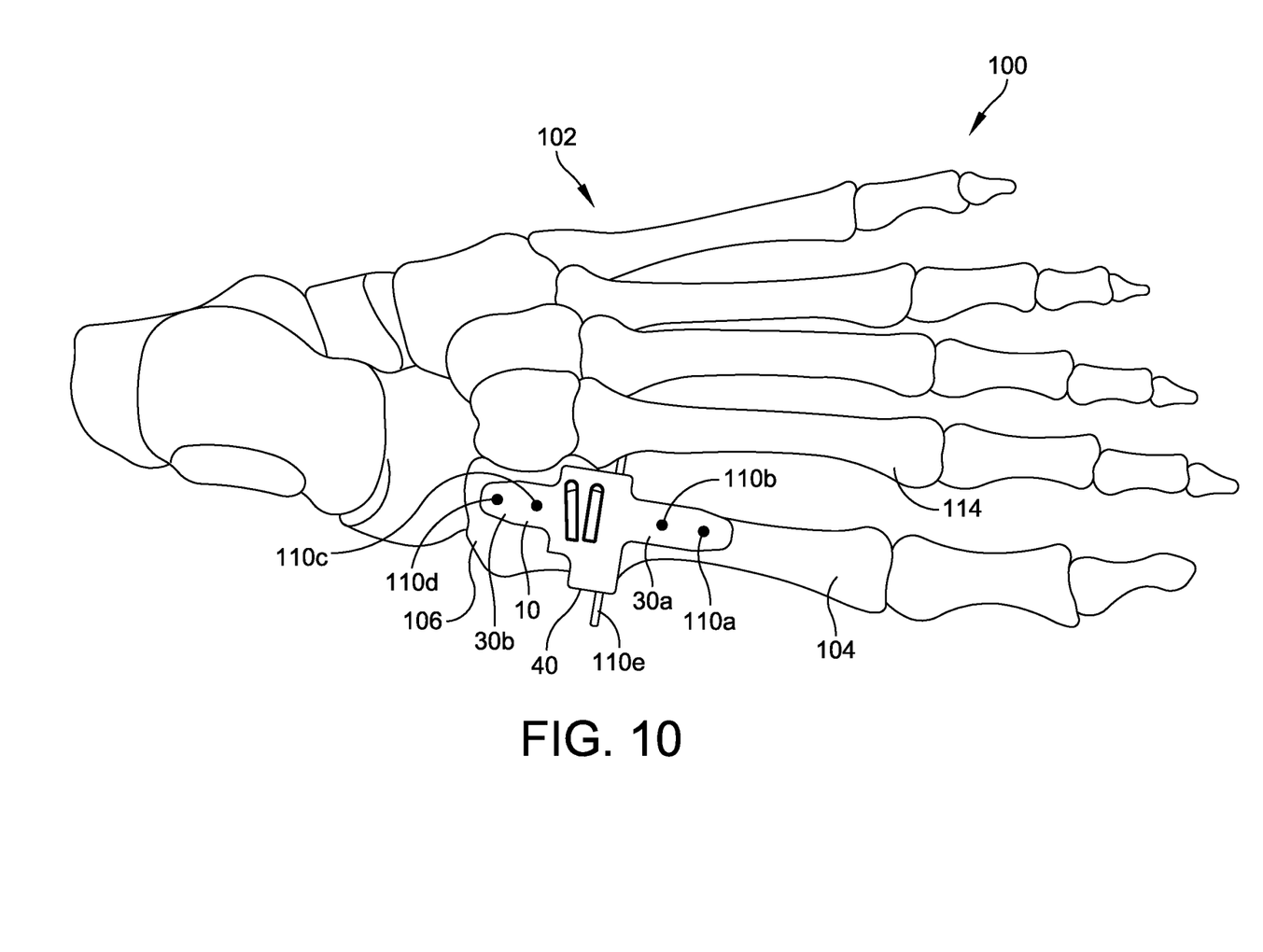
FIG. 10 illustrates a D-P view of the surgical site after rotation and compression of the second bone, in accordance with some embodiments.

At step 206, as illustrated in FIG. 10, the first metatarsal 104 is rotated and compressed with respect to the medial cuneiform 106. The first metatarsal 104 may be rotated manually and/or using a clamp or other device. The first metatarsal 104 is fixed at the rotated alignment using a fixation element, such as a third k-wire 110c, a fourth k-wire 110d, and a fifth k-wire 110e, as illustrated in FIG. 10. In some embodiments, the third k-wire 110c and the fourth k-wire 110d are inserted through respective fixation apertures 34 formed in a second coupling arm 30b of the surgical guide 10 and the fifth k-wire 110e is inserted through one of the fixation apertures 52 defined in the lateral wing 40. The fifth k-wire 110e (or other fixation element) may be inserted through the first metatarsal 104 and into a third bone, such as, for example, a second metatarsal 114.

Figure 11:
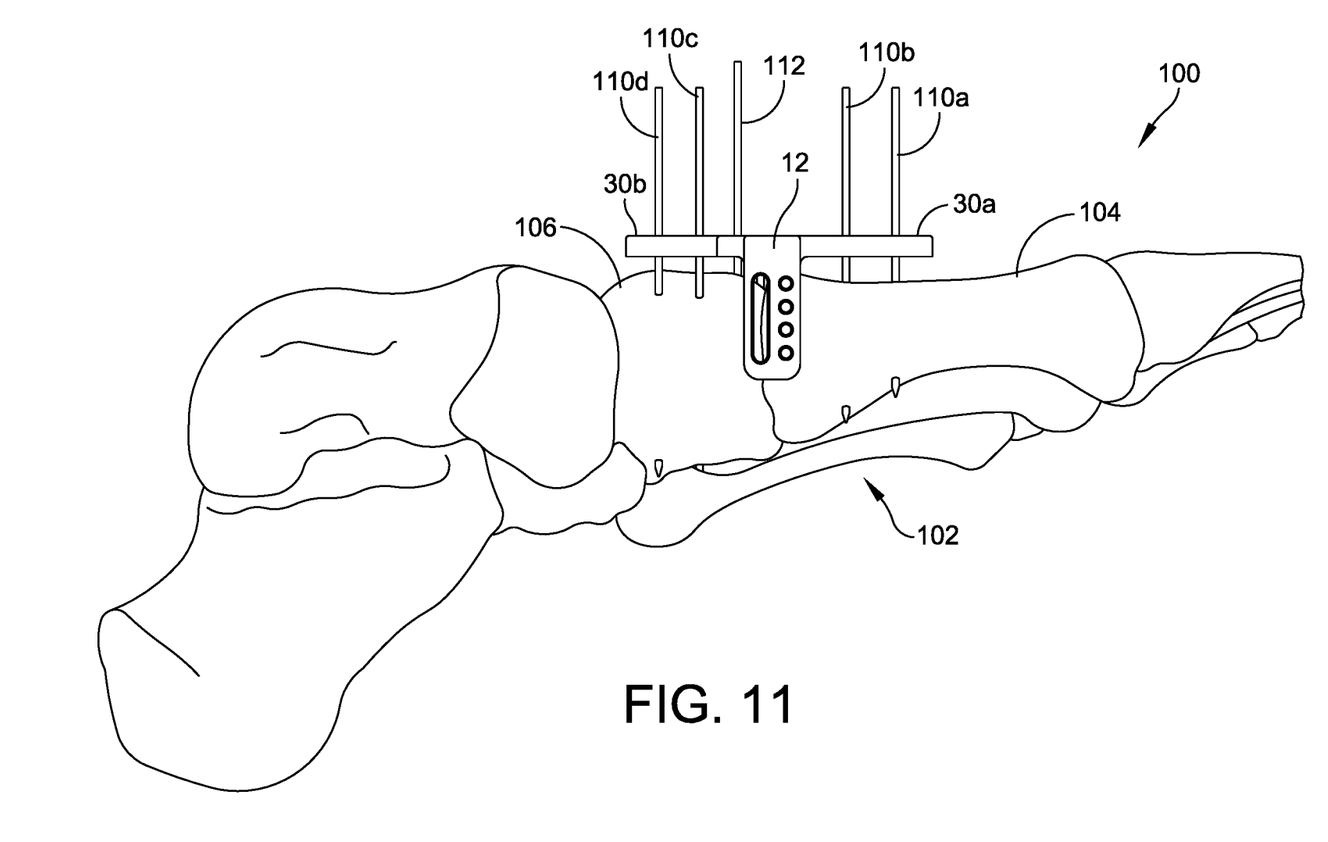
FIG. 11 illustrates a lateral view of the surgical site having the burr inserted through a second slot defined in the body of the surgical guide to remove a portion of the first bone, in accordance with some embodiments.

At step 208, as illustrated in FIG. 11, a portion of the medial cuneiform 106 is removed by inserting a cutting instrument, such as the burr 112, through a second slot 24b defined in the body 12. The second slot 24b is configured to guide the burr 112 on a predetermined path configured to form an osteotomy cut in the medial cuneiform 106. At step 210, a bone deformation is corrected and the medial cuneiform 106 is fixed using any suitable mechanism, such as, for example, an osteotomy plate.

Figure 12:
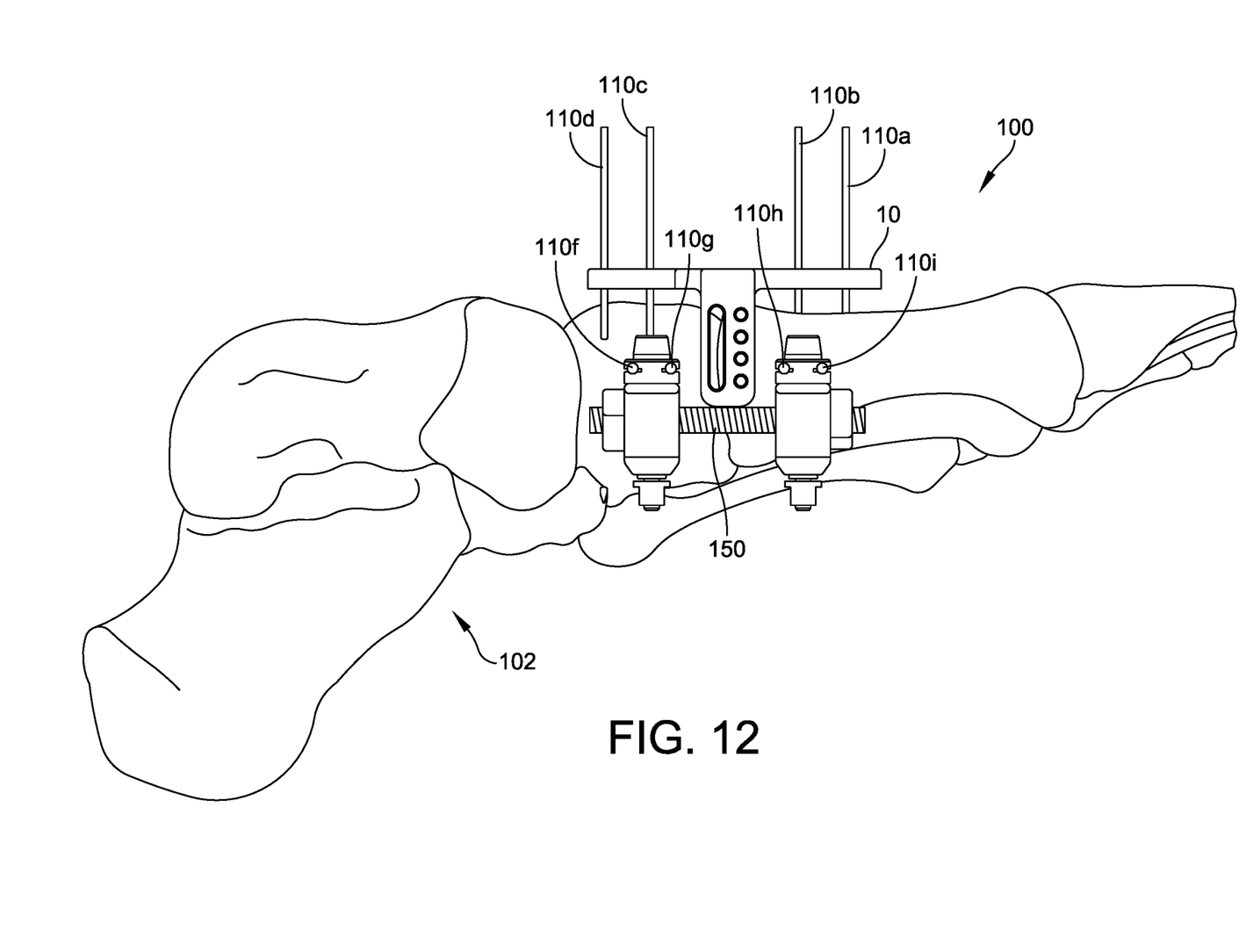
FIG. 12 illustrates a lateral view of the surgical site having a mini-rail device coupled to the first bone and the second bone, in accordance with some embodiments.
Figure 13:
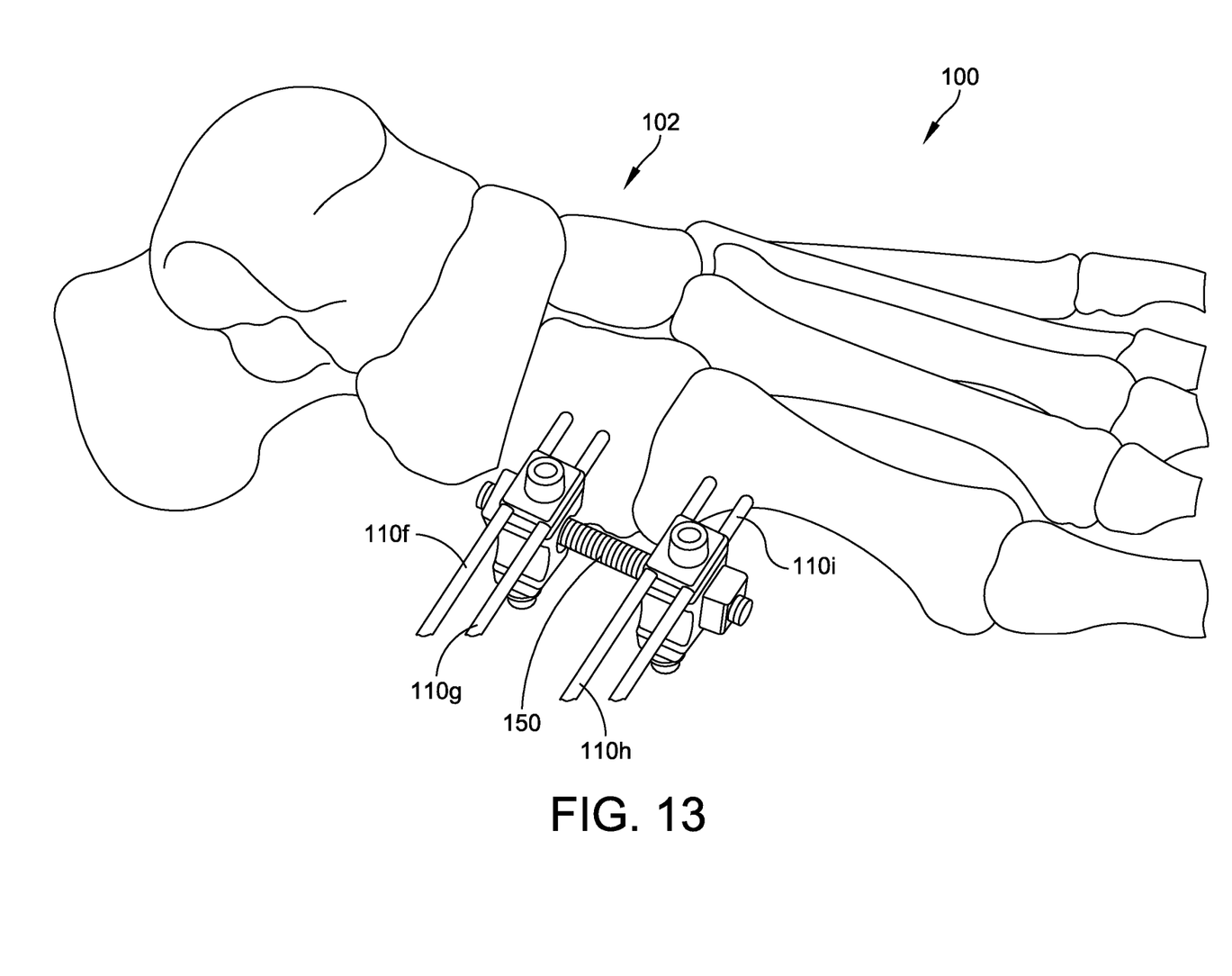
FIG. 13 illustrates the surgical site of FIG. 12 after removal of the surgical guide, in accordance with some embodiments.

In some embodiments, a mini rail external fixation device may be used in conjunction with a surgical guide 10 to form and/or maintain an osteotomy in one or more bones. As illustrated in FIG. 12, in some embodiments, a mini rail external fixation device 150 is coupled to the first metatarsal 104 and the medial cuneiform 106 to position and/or maintain the first metatarsal 104 in a rotated position as established in step 206 of the method 200. The mini rail external fixation device 150 may be coupled to the first metatarsal 104 and/or the medial cuneiform 106 by one or more fixation elements, such as, for example, a plurality of half-pins 110f-110i. After coupling, the mini rail external fixation device 150 may be used to adjust, compress, and/or maintain the first metatarsal in a fixed position with respect to the medial cuneiform using one or more methods known in the art. FIG. 13 illustrates the mini rail 150 after removal of the surgical guide 10 from the surgical site 100.

Although the subject matter has been described in terms of exemplary embodiments, it is not limited thereto. Rather, the appended claims should be construed broadly, to include other variants and embodiments, which may be made by those skilled in the art.

What is claimed is:

1. A surgical guide, comprising:
a body defining a first access port and a second access port, wherein the first access port extends on a first longitudinal axis parallel with a first edge of the body, and wherein the second access port extends on a second longitudinal axis positioned non-parallel with respect to each edge of the body;
at least one coupling arm extending from the body, wherein the at least one coupling arm defines at least one fixation aperture sized and configured to receive a fixation element through; and
at least one lateral wing extending from the body, wherein the at least one lateral wing extends substantially perpendicular to the at least one coupling arm defining at least one access port extending on a third longitudinal axis, wherein the first longitudinal axis and the third longitudinal axis define a plane parallel with the at least one edge of the body, further wherein the lateral wing defines a plurality of fixation apertures positioned substantially along a fourth longitudinal axis parallel to the third parallel axis.

2. The surgical guide of claim 1, wherein the lateral wing defines at least one fixation aperture sized and configured to receive a fixation element therethrough.

3. The surgical guide of claim 1, wherein the at least one coupling arm comprises a first coupling arm extending from the first edge of the body and a second coupling arm extending from a second edge of the body, wherein the first edge and the second edge are parallel.

4. The surgical guide of claim 1, wherein the body defines a radiolucent material, the body comprising at least one radiopaque section.

5. A system, comprising:
a surgical guide, comprising:
a body defining a first access port and a second access port, wherein the first access port extends on a first longitudinal access parallel with a first edge of the body, and wherein the second access port extends on a second longitudinal access positioned non-parallel with respect to each edge of the body;
at least one coupling arm extending from the body, wherein the at least one coupling arm defines at least one fixation aperture;
at least one lateral wing extending from the body, wherein the at least one lateral wing extends substantially perpendicular to the at least one coupling arm defining at least one access port extending on a third longitudinal axis, wherein the first longitudinal axis and the third longitudinal axis define a plane parallel with the at least one edge of the body, further wherein the lateral wing defines a plurality of fixation apertures positioned substantially along a fourth longitudinal axis parallel to the third parallel axis;
at least one fixation element sized and configured to be received within the at least one fixation aperture; and
a cutting instrument sized and configured for insertion through at least one of the first access port and the second access port.

6. The system of claim 5, the surgical guide comprising at least one lateral wing extending from the body, wherein the at least one lateral wing extends substantially perpendicular to the at least one coupling arm.

7. The system of claim 5, wherein the at least one lateral wing defines at least one access port extending on a third longitudinal axis, wherein the first longitudinal axis and the third longitudinal axis define a plane parallel with the at least one edge of the body.

8. The system of claim 5, wherein the at least one coupling arm comprises a first coupling arm extending from the first edge of the body and a second coupling arm extending from a second edge of the body, and wherein the first edge and the second edge are parallel.

9. The system of claim 5, wherein the body of the surgical guide defines a radiolucent material, the body comprising at least one radiopaque section.

10. A method of forming in osteotomy, comprising:
 coupling a surgical guide to a first bone, the surgical guide comprising a body defining a first access port and a second access port, wherein the first access port extends on a first longitudinal access parallel with a first edge of the body, and wherein the second access port extends on a second longitudinal access positioned non-parallel with respect to each edge of the body and at least one coupling arm extending from the body, wherein the at least one coupling arm defines at least one fixation aperture;
 inserting a cutting instrument through the first access port of the body to debride a joint;
 coupling the surgical guide to a second bone;
 inserting a cutting instrument through the second access port of the body to form an osteotomy in the second bone; and
 inserting a cutting instrument through a third access port defined in a lateral wing coupled to the body of the surgical guide to debride the joint, wherein the lateral wing extends from the body substantially perpendicular to the at least one coupling arm.

11. The method of claim 10, wherein the first access port and the third access port define a plane that substantially intersects the joint.

12. The method of claim 10, wherein coupling the surgical guide to the first bone comprises inserting a fixation element through a fixation aperture defined by the lateral wing.

13. The method of claim 10, comprising radioscopically imaging the surgical guide prior to insertion of the cutting instrument.

14. The method of claim 10, wherein coupling the surgical guide to the first bone comprises inserting a first fixation element through a first fixation aperture formed in the at least one coupling arm.

15. The method of claim 14, wherein the at least one coupling arm comprises a first coupling arm extending from the first edge of the body and a second coupling arm extending from a second edge of the body, wherein the first edge and the second edge are parallel, wherein the first fixation apertures is defined by the first coupling arm, and wherein coupling the surgical guide to the second bone comprises inserting a second fixation element through a second fixation aperture formed in the second coupling arm.

16. The method of claim 10, comprising coupling a mini rail device to the first bone and the second bone.

* * * * *